| United States Patent [19] | [11] 3,969,506 |
| --- | --- |
| Hardtmann | [45] July 13, 1976 |

[54] PHARMACOLOGICALLY ACTIVE TRICYCLIC QUINAZOLINONES

[75] Inventor: Goetz E. Hardtmann, Florham Park, N.J.

[73] Assignee: Sandoz, Inc., E. Hanover, N.J.

[22] Filed: Feb. 26, 1975

[21] Appl. No.: 553,143

Related U.S. Application Data

[60] Division of Ser. No. 324,996, Jan. 19, 1973, Pat. No. 3,887,559, which is a continuation-in-part of Ser. No. 163,105, July 15, 1971, abandoned, which is a continuation-in-part of Ser. No. 87,016, Nov. 4, 1970, abandoned, which is a continuation-in-part of Ser. No. 828,757, May 28, 1969, Pat. No. 3,598,823.

[52] U.S. Cl. ............................. 424/251; 424/244
[51] Int. Cl.² ........................................ A61K 31/505
[58] Field of Search ........................ 424/251, 244

[56] References Cited
UNITED STATES PATENTS

| | | | |
| --- | --- | --- | --- |
| 3,296,447 | 1/1967 | Papesch | 260/256.4 F |
| 3,468,888 | 9/1969 | Chow | 260/256.4 F |
| 3,598,823 | 8/1971 | Hardtmann | 260/256.4 |

*Primary Examiner*—Frederick E. Waddell
*Attorney, Agent, or Firm*—Gerald D. Sharkin; Richard E. Vila

[57] ABSTRACT

The compounds are biologically active tricyclic quinazolinones of the class of imidazo[2,1-b]quinazolin-5-ones, pyrimido[2,1-b]quinazolin-6-ones and diazepino[2,1-b]quinazolin-7-ones, useful, for example, as bronchodilator agents. Processes for preparation of said compounds include the reaction of a N-carboxy anthranilic anhydride (an isatoic anhydride) with a cyclic pseudothiourea such as 2-organomercapto-4,5-dihydroimidazole or 2-organomercapto-3,4,5,6-tetrahydropyrimidine.

14 Claims, No Drawings

PHARMACOLOGICALLY ACTIVE TRICYCLIC QUINAZOLINONES

This application is a division of application Ser. No. 324,996, filed Jan. 19, 1973, now U.S. Pat. No. 3,887,559, which is a continuation-in-part of now abandoned application Ser. No. 163,105, filed July 15, 1971, which in turn is a continuation-in-part of abandoned application Ser. No. 87,016, filed Nov. 4, 1970, which in turn is a continuation-in-part of application Ser. No. 828,757, filed May 28, 1969, now U.S. Pat. No. 3,598,823.

The present invention relates to tricyclic compounds which are quinazolinones, and to their preparation. The invention also relates to pharmaceutical methods and compositions for utilization of the compounds based on their biological activity.

The compound 2,3-dihydro-10-ethyl-imidazo[2,1-b]quinazolin-5(10H)-one, and a method for preparing it, are known from Doleschall et al., Acta Chim. Hung. 45, 357–360[1965]. The article contains no indication whatsoever, however, that the compound possesses pharmacological activity. The only reference to pharmacological activity in the article is to the effect that certain other related compounds were tested for activity against various viruses but were found to be inactive. I have found, however, as will be discussed in more detail hereinafter, that the compounds of the formula I hereinafter are pharmacologically active, in particular that they have, inter alia, bronchodilator activity.

The present invention in one aspect thereof provides for the effecting of pharmacological activity in animals by the administration of a compound of the formula I:

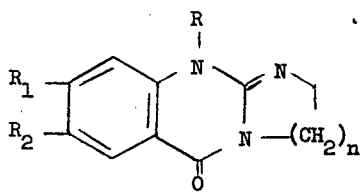

wherein
each of $R_1$ and $R_2$ is, independently, hydrogen, halo of atomic weight not greater than 36 or lower alkyl of 1 to 3 carbon atoms, or are either both hydroxy or both lower alkoxy of 1 to 2 carbon atoms; or one is hydrogen and the other bromo, hydroxy or lower alkoxy of 1 to 2 carbon atoms,
$n$ is 1 to 3; and
R is lower alkyl of 1 to 5 carbon atoms,

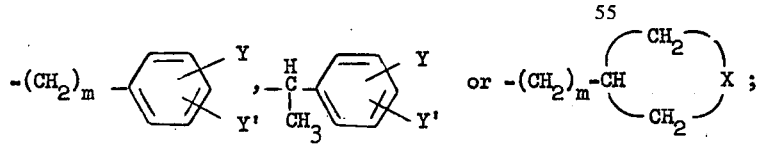

X is a direct bond or $-(CH_2)_y-$
$y$ is 1 to 3;
$m$ is 0 to 2,
each of Y and Y' is, independently, hydrogen, halo of atomic weight not greater than 36, i.e. fluoro or chloro, or lower alkyl of 1 to 3 carbon atoms, or either both are hydroxy or both are lower alkoxy of 1 to 2 carbon atoms, or one is hydrogen and the other bromo, hydroxy or lower alkoxy of 1 to 2 carbon atoms, provided that no more than two of $R_1$, $R_2$, Y and Y' are hydroxy, further provided that neither of $R_1$ and $R_2$ is hydroxy when either of Y and Y' is alkoxy and still further provided that neither of Y and Y' is hydroxy when either of $R_1$ and $R_2$ is alkoxy,
or a pharmaceutically acceptable acid addition salt thereof.

The generally preferred method for preparation of compounds of formula I involves reacting in a Step A a compound of the formula II:

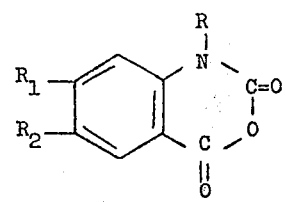

wherein $R_1$, $R_2$ and R are as defined, with a compound of formula III:

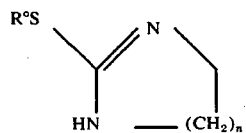

wherein $n$ is as defined and R° is lower alkyl or benzyl.

The preparation of compounds I by the reaction of Step A can be carried out at temperatures in the range of 20° to 160°C., more usually 20° to 140°C., preferably 80° to 120°C. The reaction is conveniently carried out in an organic solvent of conventional type providing an inert reaction medium. The aromatic solvents and cyclic ethers suitable for use at reflux temperatures represent the preferred solvents, e.g. toluene and dioxane. The reaction is preferably carried out in the presence of a base, e.g. sodium hydroxide or sodium carbonate; and when the compound III is employed directly in acid addition salt form, it is of course desirably to employ an amount of base somewhat greater than the amount necessary to neutralize the acid. In general, the reaction product of formula I may be recovered from the reaction of Step A by working up by conventional procedures.

The compounds of formula I other than those bearing a hydroxy substituent may also be prepared by reacting in a Step B a compound of the formula IV:

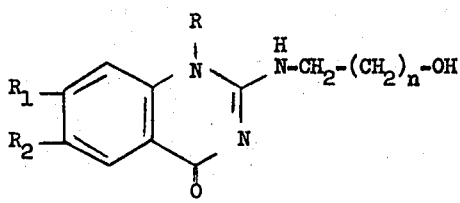

with a cyclizing agent, and treating the reaction product with an acid-binding agent.

The preparation of compounds I from compounds IV involves a cyclization of known type carried out by treating a compound IV with a reagent suitable for such type of cyclization, for example, a phosphorus halide or thionyl halide in which the halide has an atomic weight of from 35 to 80, i.e. the chloride or bromide, more preferably the chloride. The preferred reagent is thionyl chloride. The reaction with the cyclizing reagent may be carried out in absence of a solvent or in the presence of inert solvents of known type, e.g. the halogen-containing hydrocarbons such as methylene chloride and chloroform, and the aromatic solvents such as benzene and pyridine. An excess of the cyclizing agent may, however, where appropriate, be employed to provide a solvent. The treatment with an acid-binding agent, e.g., an inorganic base or tertiary amine, is preferably effected after removal of the remaining cyclizing reagent. The reaction product of formula I may be isolated from the reaction mixture by working up by established procedures.

The compounds of the formula I bearing a hydroxy substituent, i.e. one or more of $R_1$, $R_2$, Y and Y' is hydroxy, are most preferably prepared in a Step C reaction by hydrolysis of the corresponding alkoxy substituted compound of the formula I. The hydrolysis of Step C may be carried out in a conventional manner employing the usual conditions generally utilized for converting an alkoxy group to a hydroxy group, e.g. by treatment of said alkoxy compound of the formula I with aqueous hydrobromic acid at elevated temperature, e.g. 40° to 150°C.

The compounds of the formula II and III employed as starting materials in the reaction of Step A are either known or may be prepared from known materials by established procedures.

The compounds of formula IV may be prepared by reacting a compound of the formula V:

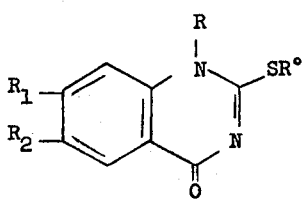

wherein R°, R, $R_1$ and $R_2$ are as defined, with a compound of formula VI:

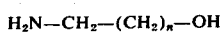

wherein $n$ is as defined.

The preparation of the compounds IV from compounds V and VI is suitably carried out at temperature in the range of from 0° to 120°C., preferably 20° to 80°C. An excess of compound VI is preferably employed. The reaction may be carried out in the absence of a solvent but is preferably conducted in the presence of an inert organic solvent which may be any of several of the well known types, preferably a chlorine-containing hydrocarbon such as chloroform and methylene chloride. The reaction product of formula IV may be isolated from the reaction mixture for use in preparation of compounds I by working up by established procedures.

The compounds of formula V may be prepared by reacting a compound of formula VII:

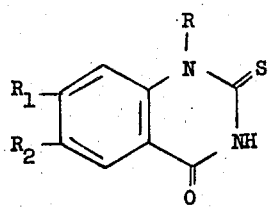

wherein R, $R_1$ and $R_2$ are as defined, with an iodo compound of formula VIII:

I—R°   VIII wherein R° is as defined.

The preparation of compounds V by reacting of compounds VII and VIII is suitably carried out at temperatures in the range of from 0°C. to 100°C., preferably 15° to 60°C. The reaction is desirably effected in the presence of an inert organic solvent which may be any of several well known types, preferably a lower alcohol of 1 to 5 carbon atoms or an ether, e.g., ethanol and dioxane, preferably ethanol. The reaction product of formula V may be isolated from the reaction mixture for use in preparation of compounds IV by working up by established procedures.

The compounds of the formulae VII and VIII are either known or may be prepared from known materials by established procedures.

Also within the scope of the compounds of formula I of the invention are pharmaceutically acceptable salts not materially depreciating the pharmacological effect of the compounds. Such salts include the acid addition salts of known type, e.g., the hydrochloride. The acid addition salts may be produced from the corresponding free bases by conventional procedures. Conversely, the free bases may be obtained from the salts by procedures known in the art.

The compounds of formula I of the invention are useful because they possess biological activity. In general, the compounds possess in animals one or more pharmacological activities such as bronchodilator activity, hypotensive activity, and central nervous system activity. In particular, the compounds of the formula I in which R is alkyl or a phenyl or substituted phenyl ring separated from the ring nitrogen by an alkylene moiety, i.e. the compounds of the following formulae Ia, Ib and Ic:

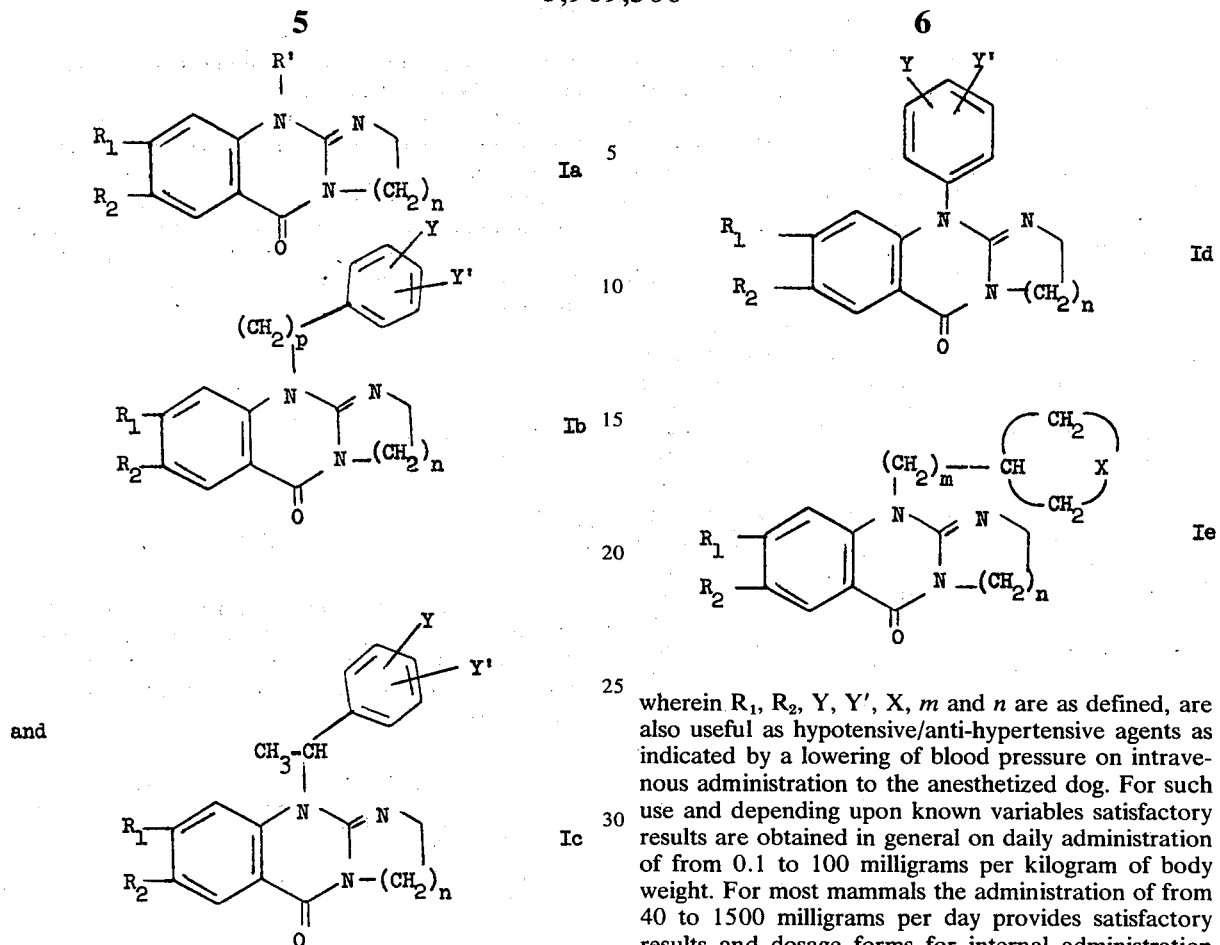

which $R_1$, $R_2$, Y, Y' and n are as defined and p is 1 or 2 and R' is alkyl of 1 to 5 carbon atoms are useful as bronchodilator agents as indicated by measuring bronchial resistance on intravenous administration (0.1–5 mgs./kgs.) in the anesthetized guinea pig and according to the test of Konzett and Rossler, Arch. Exp. Path. and Pharmak. 195:71 (1940); and by observing the respiratory status on oral administration (0.5–100 mgs./kgs.) to the unanesthetized guinea pig exposed to aerosolized histamine dihydrochloride according to a modification of the method of Van Arman et al., J. Pharm. pharmacol. Exptl. Therap. 133:90–97, 1961; and in vitro by observing the effect (0.1–30 micrograms/ml.) on strips of guinea pig trachea according to the method of Constantine, J. Pharm. Pharmacol. 17: 384–385, 1960. For such use and depending upon known variables satisfactory results are obtained in general on the daily administration of from 0.3 to 100 milligrams per kilogram of body weight, preferably given in divided doses 2 to 4 times a day, or in sustained release form. For most mammals the administration of from 20 to 1500 milligrams per day provides satisfactory results and dosage forms suitable for internal administration comprise 5 to 950 milligrams of the compound in admixture with a solid or liquid pharmaceutical carrier or diluent.

The compounds of the formula I in which R is phenyl or substituted phenyl or cycloalkyl or cycloalkylalkyl, i.e. the compound of the following formulae Id and Ie:

wherein $R_1$, $R_2$, Y, Y', X, m and n are as defined, are also useful as hypotensive/anti-hypertensive agents as indicated by a lowering of blood pressure on intravenous administration to the anesthetized dog. For such use and depending upon known variables satisfactory results are obtained in general on daily administration of from 0.1 to 100 milligrams per kilogram of body weight. For most mammals the administration of from 40 to 1500 milligrams per day provides satisfactory results and dosage forms for internal administration comprise from 10 to 750 milligrams in combination with a suitable carrier. The preferred compounds for effecting a lowering of blood pressure are those in which R is cycloalkylalkyl, n is 1 or 2 and $R_1$ and $R_2$ are hydrogen, more preferably R is cyclopropylmethyl and/or n is 1.

The preferred compounds of the invention from the standpoint of bronchodilator activity, e.g. in the histamine aerosol assay, are those in which R is benzyl including substituted benzyl, particularly unsubstituted benzyl and more particularly those which have one or two fluoro substituents on the benzyl moiety, especially one, or have a 4-halo substituted-benzyl, and the more preferred such compounds are those in which each of $R_1$ and $R_2$ is hydrogen, and those in which n is 1 or 2, e.g. 10-benzyl-2,3-dihydro-imidazo[2,1-b]quinazolin-5(10H)-one. The especially preferred such bronchodilators from the standpoint of exhibiting exceptional activity are those in which R is 4-halobenzyl (i.e. 4-fluoro-, 4-chloro- and 4-bromobenzyl), particularly those in which n is 1, e.g. 10-(4-chlorobenzyl)-2,3-dihydro-imidazo[3,1-b]quinazolin-5(10H)-one and 10-(4'-fluorobenzyl)-2,3-dihydro-imidazo[2,1-b]quinazolin-5(10H)-one.

The compounds of the invention in which at least one of $R_1$ and $R_2$ is halo and/or R is phenyl including substituted phenyl also exhibit Central Nervous System activity. Thus, the compounds of the formula I in which n is 1 and at least one of $R_1$ and $R_2$ is halo and those in which n is 1 and R is phenyl including substituted phenyl, as represented by the compounds of Examples 2A and 13A hereinafter, are also indicated as useful as anti-depressants by effecting a reversal of reserpine hypothermia in mice. For this use the compounds may be administered generally to animals at a daily dose of from 1 to 75 milligrams per kilogram of body weight with the daily dosage for most mammals being in the range of 75 to 1000 milligrams, and with divided doses containing about 18 to 500 milligrams.

In addition, the compounds of the formula I in which R is alkyl, at least one of $R_1$ and $R_2$ is halo and $n$ is 2 or 3, as represented by the compounds of Examples 1 and 2 are also indicated as useful as analeptic agents by having a CNS stimulant effect in behavior tests in mice and by effecting an antagonism of hexobarbital anesthesia in mice. For this use satisfactory results are obtained on the administration of from 0.5 to 50 milligrams per kilogram of body weight (i.v.), and the dosage for most mammals is in the range of from 35 to 500 milligrams i.v.p.r.n. Also, the compound of Example 13B is indicated as useful as a tranquilizer/sedative by exhibiting a mixed CNS response in behavior tests in mice and by exhibiting in animals an antagonism to amphetamine in mice and a reinduction of hexobarbital in mice. For such usage satisfactory results may be obtained in general at daily dosages of from 4 to 100 milligrams per kilogram of animal body weight with the daily dose for most mammals being in the range of about 300 to 3000 milligrams.

Apart from the analeptic use indicated above, the compounds may be combined with a pharmaceutically acceptable carrier, and such other conventional adjuvants as may be necessary, and administered orally or parenterally. For most uses, oral administration with carriers is preferred and may take place in such conventional forms as tablets, dispersible powders, granules, capsules, suspensions, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxy-benzoate). Capsules may contain the active ingredient alone or admixed with an inert solid diluent, e.g., calcium carbonate, calcium phosphate and kaolin. The preferred pharmaceutical compositions from the standpoint of preparation and ease of oral administration are solid compositions, particularly hard-filled capsules and tablets. Parenteral administration may be in such conventional forms as injectionable solutions and suspensions and may be preferred or required in certain situations as will be evident, for example, when desiring to employ certain of the above-indicated compounds as analeptic agents.

A representative formulation is a tablet for oral administration 2 to 4 times a day for prophylatic treatment of bronchial asthma and prepared by conventional tabletting techniques to contain the following ingredients:

| Ingredients | Weight (mg.) |
| --- | --- |
| 10-(4'-fluorobenzyl)-2,3-dihydro-imidazo[2,1-b]quinazolin-5(10H)-one | 25 |
| Tragacanth | 10 |
| Lactose | 222.5 |
| Corn Starch | 25 |
| Talcum | 15 |
| Magnesium Stearate | 2.5 |

A representative formulation is also a capsule for oral administration 2 to 4 times a day for prophylatic treatment of bronchial asthma and prepared by conventional capsulating techniques to contain the following ingredients:

| Capsule Ingredients | Weight (Mg.) |
| --- | --- |
| 10-(4'-fluorobenzyl)-2,3-dihydro-imidazo[2,1-b]quinazolin-5(10H)-one | 10 |
| Lactose | 316 |
| Sterotex K (a triglycerol ester lubricant) | 10 |

In addition, the compounds of the formula I may be administered as bronchodilators by inhalation therapy in a conventional manner, e.g., by the use of nebulizers, vaporizers, aerosols and the like. Compositions for use in administration by inhalation therapy may be prepared accordingly to conventional procedures and contain the usual conventional ingredients employed in such compositions. A representative aerosol formulation prepared by conventional techniques for use with a metered value system contains the following ingredients:

| | |
| --- | --- |
| 10-(4'-fluorobenzyl)-2,3-dihydro-imidazo[2,1-b]quinazolin-5(10H)-one | 0.4 – 20% |
| Ethyl alcohol | 10 – 40% |
| Ascorbic acid | 1 – 10% |
| Freon 11 | 10 – 30% |
| Freon 114 | 10 – 30% |
| Freon 12 | 30 – 60% |
| Buffer System - pH control | q.s. |
| Flavor | q.s. |

A representative formulation is a tablet for oral administration two to four times a day for effecting a reduction in blood pressure and prepared by conventional tabletting techniques to contain the following ingredients:

| Ingredients | Weight (mg.) |
| --- | --- |
| 10-cyclopropyl-2,3-dihydro-imidazo[2,1-b]quinazolin-5(10H)-one | 25 |
| Tragacanth | 10 |
| Lactose | 222.5 |
| Corn Starch | 25 |
| Talcum | 15 |
| Magnesium Stearate | 2.5 |

A representative formulation is also a capsule for oral administration 2 to 4 times a day for prophylatic treatment of bronchial asthma and prepared by conventional capsulating techniques to contain the following ingredients:

| Capsule Ingredients | Weight (Mg.) |
|---|---|
| 10-cyclopropyl-2,3-dihydro-imidazo[2,1-b]quinazolin-5(10H)-one | 10 |
| Lactose | 316 |
| Sterotex K (a triglycerol ester lubricant) | 10 |

The following examples show representative compounds encompassed within the scope of this invention and the manner in which such compounds are prepared. However, it is to be understood that the examples are for purposes of illustration only.

EXAMPLE 1

11-Methyl-8-chloro-2,3,4,11-tetrahydropyrimido[2,1-b]quinazolin-6-one

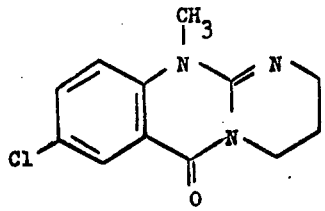

A mixture of 12.5 g. of 6-chloro-N-methylisatoic anhydride, 6.5 g. of 2-methylmercapto-3,4,5,6-tetrahydropyrimidine and one pellet of sodium hydroxide is refluxed in 200 ml. of dioxane for 18 hours. The cooled mixture is filtered through Celite and most of the solvent is evaporated. The residue is taken up in methylene chloride, the solution extracted with water, dried, treated with charcoal and evaporated to obtain an oily residue which is crystallized from diethyl ether to obtain 11-methyl-8-chloro-2,3,4,11-tetrahydropyrimido[2,1-b]quinazolin-6-one, m.p. 119°–120°C. Additional amounts of this product could be obtained by working up the mother liquor by chromatography on silica gel and thereafter crystallizing from methylene chloride containing 5% methanol.

EXAMPLE 2

The following compounds of the invention are prepared employing the reaction which is exemplified in Example 1.

A. 7-chloro-2,3-dihydro-10-methyl-imidazo[2,1-b]quinazolin-5(10H)-one, m.p. 200°–202°C.
B. 9-chloro-12-methyl-2,3,4,5-tetrahydro(12H)-diazepino[2,1-b]quinazolin-7-one, m.p. 118°–119°C.
C. 2,3-dihydro-10-methyl-imidazo[2,1-b]quinazolin-5(10H)-one, m.p. 213°–215°C.
D. 8-chloro-2,3-dihydro-10-methyl-imidazo[2,1-b]quinazolin-5-(10H)-one, m.p. 277°–279°C.
E. 7,8-dimethoxy-2,3-dihydro-10-methyl-imidazo[2,1-b]quinazolin-5(10H)-one, 253°–256°C.
F. 2,3-dihydro-10-ethyl-7-chloro-imidazo[2,1-b]quinazolin-5(10H)-one, m.p. 154°–156°C.
G. 7-chloro-2,3-dihydro-10-benzyl-imidazo[2,1-b]quinazolin-5(10H)-one, m.p. 189°–191°C.
H. 7,8-dimethoxy-2,3-dihydro-10-benzyl-imidazo[2,1-b]quinazolin-5(10H)-one, m.p. 187°–189°C.
I. 11-benzyl-2,3,4,11-tetrahydropyrimido[2,1-b]quinazolin-6-one, m.p. 158°–160°C.
J. 2,3-dihydro-10-ethyl-imidazo[2,1-b]quinazolin-5(10H)-one.
K. 8-chloro-10-benzyl-2,3-dihydro-imidazo[2,1-b]quinazolin-5(10H)-one methanesulfonate, m.p. 251°–253°C.
L. 12-benzyl-2,3,4,5-tetrahydro-(12H)-diazepino[2,1-b]quinazolin-7-one, m.p. 103°–105°C.
M. 10-isopropyl-2,3-dihydro-imidazo[2,1-b]quinazolin-5(10H)-one, m.p. 149°–151°C.

EXAMPLE 3

2,3-Dihydro-10-benzyl-imidazo[2,1-b]quinazolin-5(10H)-one

A mixture of 12.7 g. of N-benzylisatoic anhydride, 5.8 g. of 2-methylmercapto-imidazoline and 2 pellets of sodium hydroxide in 200 ml. of dioxane was refluxed for 2 hours. While still hot, the mixture was then filtered through Celite and the filtrate concentrated to about 50 ml. volume. 50 ml. of diethyl ether was added and the crystalline precipitate removed by filtration. The residue was dissolved in methylene chloride, treated with charcoal, filtered through alumina, and the filtrate evaporated. The residue was crystallized from methylene chloride/diethyl ether to obtain the heading compound, m.p. 203°–205°C.

EXAMPLE 4

7-Chloro-2,3-dihydro-10-methyl-imidazo[2,1-b]quinazolin-5(10H)-one (alternative procedure)

Step (a) 6-Chloro-1-methyl-2-methylmercapto-4-quinazolinone

A mixture of 35 g. of 6-chloro-1-methyl-2-thioquinazoline-2,4-dione, 500 ml. ethanol and 50 g. of methyl iodide is stirred at room temperature for 48 hours. The ethanol is evaporated off in vacuo to obtain a crude oil of 6-chloro-1-methyl-2-methylmercapto-4-quinazolinone.

Step (b) 6-Chloro-1-methyl-2-(2-hydroxyethyl)amino-4-quinazolinone 38 g. of the crude product obtained in (a) above is added to a solution of 95 g. of ethanolamine in 200 ml. of chloroform. The resulting mixture is stirred for 3 hours at room temperature and then warmed to 60°C. for 30 minutes while maintaining the stirring. The chloroform is then evaporated off in vacuo, the residue poured onto 500 g. of ice-water and the resulting system extracted 4 times each time with 300 ml. of methylene chloride. The combined organic phase is washed 3 times with water and 3 times with saturated sodium chloride solution, dried, and evaporated in vacuo. The residue is then treated 3 times with toluene which is evaporated off in vacuo after each treatment to obtain a crude residue of 6-chloro-1-methyl-2-(2-hydroxyethyl)amino-4-quinazolinone.

Step (c) 7-Chloro-2,3-dihydro-10-methyl-imidazo[2,1-b]quinazolin-5(10H)-one 11 g. of the crude product obtained in (b) above is dissolved in 30 ml. of thionyl chloride and the resulting mixture heated at 80°C. for 3 hours. The solvent is evaporated in vacuo and the residue is dissolved in methylene chloride, extracted with sodium bicarbonate solution and then with water, the organic phase dried, evaporated in vacuo and the residue crystallized from methylene chloride/diethyl ether to obtain 7-chloro-2,3-dihydro-10-methyl-imidazo[2,1-b]quinazolin-5(10H)-one, m.p. 200°–202°C.

EXAMPLE 5

2,3-Dihydro-10-benzyl-imidazo[2,1-b]quinazolin-5(10H)-one (alternative procedure)

Step (a) 1-Benzyl-2-thio-1,2,3,4-tetrahydroquinazolin-4-one

A suspension of 75 g. of N-benzylanthranilic acid in 500 ml. of pyridine was added portionwise over an hour to a boiling solution of 32 g. of ammonium thiocyanate and 47 ml. of benzoyl chloride in 120 ml. of anhydrous acetone. The mixture was cooled and concentrated. The residue was mixed with 250 ml. of methanol and the crystalline precipitate was filtered and washed with water to obtain the heading compound.

Step (b) 1-Benzyl-2-methylmercapto-1,4-dihydroquinazolin-4-one

A mixture of 5 g. of the product obtained in (a) above, 40 ml. of ethanol and 4 ml. of methyl iodide was stirred at room temperature for 3 hours. 4 ml. of 6N potassium hydroxide was added and the mixture allowed to stand overnight. The precipitate was then filtered off, and washed with water, ethanol and ether to obtain the heading compound.

Step (c) 1-Benzyl-2-(2-hydroxyethyl)amino-4-quinazolinone

A mixture of 2.8 g. of the crude product from (b) above, 15 ml. of ethanolamine and 40 ml. of chloroform was stirred at room temperature for 2 hours. The mixture was then heated at 60°C. for 1 hour. The solvent was then evaporated off in vacuo, and the residue dissolved in ethyl acetate/benzene (1:1) and extracted three times with water. The organic phase was dried and evaporated in vacuo to obtain a crude residue of the heading compound.

Step (d) 2,3-Dihydro-10-benzyl-imidazo[2,1-b]quinazolin-5(10H)-one 0.5 g. of the crude product obtained in (c) above was dissolved in 10 ml. of thionyl chloride, and the resulting mixture heated at 80°C. for 2 hours. The thionyl chloride was evaporated in vacuo, the residue treated with ice-6N sodium hydroxide solution and the solid dissolved in methylene chloride followed by extraction with water and with saturated sodium chloride solution. After drying and evaporation in vacuo, the residue was crystallized from ether to obtain the heading compound, m.p. 203°–204°C.

EXAMPLE 6

10-(4'-fluorobenzyl)-2,3-dihydro-imidazo[2,1-b]Quinazolin-5(10H)-one

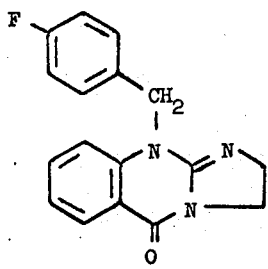

Step A: Preparation of N-(p-fluorobenzyl)isatoic anhydride

To a solution of 16.3 g. of isatoic anhydride in 200 ml. of dimethylacetamide at room temperature is added sodium hydride obtained from 5.0 g. of 57% solution in mineral oil. The resulting mixture is stirred for 20 minutes and 16 g. of p-fluorobenzyl chloride is added followed by stirring at room temperature for about 15 hours. The resulting mixture is concentrated in vacuo to about one half its volume, a mixture of ice and water added and the resulting precipitate filtered off, washed with water, dried under suction and washed with pentane. The solid material is then dissolved in methylene chloride, dried with sodium sulfate, treated with charcoal and about twice the volume of diethyl ether added to crystallize N-(p-fluorobenzyl)isatoic anhydride, m.p. 142°–145°C.

Step B: Preparation of 10-(4'-fluorobenzyl)-2,3-dihydro-imidazo[2,1-b]quinazolin-5(10H)-one A solution of 5.4 g. of N-(p-fluorobenzyl)isatoic anhydride, 2.5 g. of 2-methylmercapto-imidazoline and one pellet (about 100 mg.) sodium hydroxide in 75 ml. of dioxane is refluxed with stirring for 4 hours. The resulting mixture is evaporated to dryness, the residue dissolved in methylene chloride, washed with water and extracted twice with 1N hydrochloric acid. The combined aqueous extracts are washed with methylene chloride and then with diethyl ether and made basic with sodium bicarbonate. The resulting precipitate is filtered off, washed thoroughly with water, dried by suction, dissolved in methylene chloride, dried with sodium sulfate, treated with charcoal and the methylene chloride exchanged for methanol to crystallize 10-(4'-fluorobenzyl)-2,3-dihydro-imidazo[2,1-b]quinazolin-5(10H)-one, m.p. 192°–195°C.

EXAMPLE 6A

A suspension of the final product of Example 3 in the amount of 3.6 g. in 30 ml. of absolute ethanol is saturated with anhydrous hydrogen chloride under ice cooling to form a solution which is concentrated in vacuo to one half its volume, charcoal added and the solution filtered through celite. About 50 ml. of diethyl ether is then added to crystallize 10-(4'-fluorobenzyl)-2,3-dihydro-imidazo[2,1-b]quinazolin-5(10H)-one hydrochloride, melting at 235°–238°C. and again at about 320°C.

EXAMPLE 7

The following additional compounds of the invention are prepared employing the reactions exemplified in Examples 6 and 6A:

A. 11-(3',4'-dimethoxybenzyl)-2,3,4-11-tetrahydropyrimido[2,1-b]quinazolin-6-one, m.p. 142°–144°C.

B. 10-(4'-methylbenzyl)-2,3-dihydro-imidazo[2,1-b]quinazolin-5(10H)-one methanesulfonate, m.p. 207°–210°C.

C. 10-(2'-methylbenzyl)-2,3-dihydro-imidazo[2,1-b]quinazolin-5(10H)-one methanesulfonate, m.p. 257°–260°C.

D. 10-phenethyl-2,3-dihydroimidazo[2,1-b]quinazolin-5(10H)-one methanesulfonate, m.p. 237°–239°C.

E. 10-(3',4'-dimethoxybenzyl)-2,3-dihydro-imidazo[2,1-b]quinazolin-5(10H)-one methanesulfonate, m.p. 180°–182°C.

F. 10-(α-methyl-benzyl)-2,3-dihydro-imidazo[2,1-b]quinazolin-5(10H)-one, m.p. 136°–138°C.

G. 10-benzyl-7-methoxy-2,3-dihydro-imidazo[2,1-b]quinazolin-5(10H)-one, m.p. 173°–175°C.

H. 10-(3',4'-dimethoxybenzyl)-2,3,4,5-tetrahydro-(12H)-diazepino[2,1-b]quinazolin-7-one, m.p. 134°–136°C.

I. 11-(4'-fluorobenzyl)-2,3,4,11-tetrahydropyrimido[2,1-b]quinazolin-6-one, m.p. 154°–156°C.

J. 8-chloro-10-(4'-fluorobenzyl)-2,3-dihydro-imidazo[2,1-b]quinazolin-5(10H)-one, m.p. 174°–176°C.

K. 10-(3'-fluorobenzyl)-2,3-dihydro-imidazo[2,1-b]quinazolin-5(10H)-one hydrochloride, m.p. 262°–264°C.

L. 10-(2'-fluorobenzyl)-2,3-dihydro-imidazo[2,1-b]quinazolin-5(10H)-one hydrochloride, m.p. 251°–255°C.

M. 10-(4'-chlorobenzyl)-2,3-dihydro-imidazo[2,1-b]quinazolin-5(10H)-one, m.p. 225°–227°C.

N. 10-(3',4'-difluorobenzyl)-2,3-dihydro-imidazo[2,1-b]quinazolin-5(10H)-one, m.p. 209°–211°C.

O. 10-(4'-bromobenzyl)-2,3-dihydro-imidazo[2,1-b]quinazolin-5(10H)-one, m.p. 175°–177°C.

P. 10-(2',6'-dichlorobenzyl)-2,3-dihydro-imidazo[2,1-b]quinazolin-5(10H)-one, m.p. 164°–166°C.

Q. 11-(4'-chlorobenzyl)-2,3,4,11-tetrahydropyrimido[2,1-b]quinazolin-6-one, m.p. 178°–180°C.

R. 10-(2'-chlorobenzyl)-2,3-dihydro-imidazo[2,1-b]quinazolin-5(10H)-one, m.p. 250°–252°C.

S. 10-(4'-fluorobenzyl)-2,3-dihydro-imidazo[2,1-b]quinazolin-5(10H)-one, m.p. 211°–214°C.

T. 10-isopentyl-2,3-dihydro-imidazo[2,1-b]quinazolin-5(10H)-one, m.p. 103°–105°C.

U. 10-(4'-methoxybenzyl)-2,3-dihydro-imidazo[2,1-b]quinazolin-5(10H)-one hydrochloride, m.p. 228°C. (decomp.).

EXAMPLE 8

10-Benzyl-7-hydroxy-2,3-dihydro-imidazo[2,1-b]quinazolin-5(10H)-one

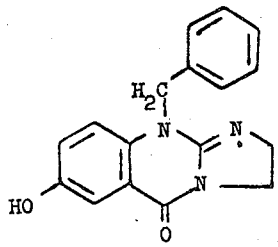

One gram of 10-benzyl-7-methoxy-2,3-dihydro-imidazo[2,1-b]quinazolin-5(10H)-one is added slowing to 10 ml. of 48% hydrobromic acid and the resulting mixture refluxed with stirring for 2 hours. The resulting mixture is cooled and the precipitated material filtered off and dissolved in 1N. sodium hydroxide. The resulting solution is washed twice with methylene chloride and slowly acidified to about pH6 with 2N hydrochloric acid to form a crystalline material which is filtered off, washed with water, dried by suction and dissolved in chloroform and a minor amount of methanol, treated with charcoal and concentrated on a steam bath to crystallize 10-benzyl-7-hydroxy-2,3-dihydro-imidazo[2,1-b]quinazolin-5(10H)-one, m.p. 225°–227°C.

EXAMPLE 9

10-(4'-fluorobenzyl)-2,3-dihydro-imidazo[2,1-b]quinazolin-5(10H)-one

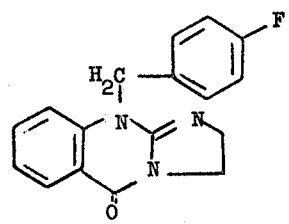

Step A: Preparation of N-(p-fluorobenzyl)isatoic anhydride

To a solution of 3.2 kgs. isatoic anhydride in 15 kgs. dimethylacetamide is added under nitrogen with stirring sodium hydride obtained from 880 gms. of a 57% dispersion in mineral oil, while maintaining the temperature below 25°C. The resulting mixture is heated to about 60°C. and held at about 55°–60°C. for 1 hour. The reaction mixture is then cooled to 20°–30°C. and to it is added 3.0 kgs. p-fluorobenzyl chloride. The mixture is then reheated to about 60°C. and held there for about 4 hours. It is then cooled again to 20°C. and to it is added 17.4 kgs. of ice and then 24 kgs. water. The mixture is stirred for 15 minutes, the solids collected by filtration, washed with several 2 kg. portions of water and then three times with 0.7 kg. diethylether. The washed solids are dried to obtain N-(p-fluorobenzyl)isatoic anhydride, m.p. 140°–143°C.

Step B: Preparation of 10-(4'-fluorobenzyl)-2,3-dihydroimidazo[2,1-b]quinazolin-5(10H)-one A charge of 26 kgs. toluene, 2.5 kgs. 2-methylmercaptoimidazoline hydroiodide, 2.4 kgs. N-(p-fluorobenzyl)isatoic anhydride and 1.55 kgs. powdered anhydrous sodium carbonate is refluxed for 18 – 20 hours in a reaction vessel which is vented to a caustic gas washing tower. Any water formed during the reaction is collected in a Dean-Stark separator. The reaction is cooled to 20°C. and 10 kgs. water added. The mixture is stirred for about 30 minutes and the solids collected, washed several times with 2 kg. portions of water, and three times with 0.8 kg. toluene. The solids are then dried at reduced pressure (about 55°C.) to obtain a crude product, m.p. 196°–198°C. The crude is dissolved at 50°C. in a solution of 14 kgs. chloroform and 4 kgs. ethanol and treated in solution with 0.1 kg. decoloring charcoal for about 10 minutes. The charcoal is removed by filtration through a celite bed and solids reprecipitated by concentrating the filtrate to a volume of about 8 liters. This concentrate is cooled to 0°–5°C., the solids collected by filtration, washed with cold ethanol and then diethyl ether, and dried at reduced pressure to obtain 10-(4'-fluorobenzyl)-2,3-dihydro-imidazo[2,1-b]quinazolin-5(10H)-one, m.p. 197°–198°C.

EXAMPLE 10

10-cyclopropylmethyl-2,3-dihydro-imidazo[2,1-b]quinazolin-5(10H)-one maleate 3,969,506

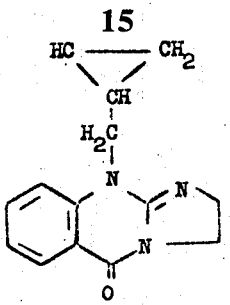

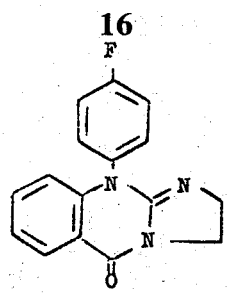

Step A: Preparation of N-(cyclopropyl)isatoic anhydride

To a solution of 20 g. isatoic anhydride in 200 ml. dimethylacetamide is added under nitrogen with stirring sodium hydride obtained from 6 g. of a 57% dispersion in mineral oil, while maintaining the temperature below 25°C. The resulting mixture is stirred at 25°C. for 1 hour and to it is added 17 g. cyclopropylmethylbromide. The mixture is then stirred at room temperature for about 20 hours. It is then poured on water. The mixture is stirred for 15 minutes, the solids collected by filtration, washed with several portions of water and then three times with 0.7 kg. of diethylether. The washed solids are dried to obtain N-(cyclopropylmethyl)isatoic anhydride, m.p. 118°–121°C.

Step B: Preparation of 10-cyclopropylmethyl-2,3-dihydroimidazo[2,1-b]quinazolin-5(10H)-one A charge of 100 ml. of dioxane, 3.5 g. 2-methylmercaptoimidazoline hydroiodide, 6 g. N-(cyclopropylmethyl)isatoic anhydride and 2 pellets of sodium hydroxide is refluxed for 1 hour in a reaction vessel. The reaction is cooled to 20°C. and the solvent evaporated. The residue is dissolved in methylene chloride and this solution is extracted with 1 normal hydrochloride solution. The acid solution is extracted with methylene chloride (discard) and with ether (discard) and then made basic with 10% sodium bicarbonate solution. The precipitate which forms is filtered off, washed with water and dissolved in methylene chloride. After drying with anhydrous sodium sulfate, the solvent is exchanged from ether and the product crystallized by additon of pentane. This material is converted into its hydrogen maleate addition salt by conventional procedures to obtain 10-cyclopropylmethyl-2,3-dihydroimidazo[2,1-b]quinazolin-5(10H)-one hydrogen maleate, m.p. 189°–192°C.

EXAMPLE 11

The following additional compounds of the invention are prepared employing the reactions exemplified in Examples 1 and 2:

A. 10-cyclopropyl-2,3-dihydro-imidazo[2,1-b]quinazolin-5(10H)-one.
B. 10-cyclohexyl-2,3-dihydro-imidazo[2,1-b]quinazolin-5(10H)-one, m.p. 196°–198°C.
C. 10-cyclohexylethyl-2,3-dihydro-imidazo[2,1-b]quinazolin-5(10H)-one, m.p. 139°–141°C.
D. 10-cyclohexylmethyl-2,3-dihydro-imidazo[2,1-b]quinazolin-5(10H)-one, m.p. 142°–149°C.
E. 10-cyclopropylmethyl-2,3-dihydro-imidazo[2,1-b]quinazolin-5(10H)-one, m.p. 140°–143°C.

EXAMPLE 12

10-p-Fluoro-phenyl-2,3-dihydro-imidazo[2,1-b]quinazolin-5(10H)-one

Step A: Preparation of N-(p-Fluoro-phenyl)isatoic anhydride

The potassium salt of o-chlorobenzoic acid (25 g), 25 g. of 4-fluoroaniline, 9 g. potassium carbonate and 2 g. of copper powder were heated under reflux in 200 ml. dimethylformamide. After cooling the solvent was evaporated, the residue dissolved in 500 ml. of absolute ethanol, the solution was filtered and the filtrate evaporated. The residue was suspended in 300 ml. of methylene chloride and filtered. The solid (on 10 filter) was dissolved in 100 ml. of water and 45 g. of potassium carbonate was added. To this solution 65 ml. phosgene (12.5% in benzene) was added under vigorous stirring. The stirring was continued for 18 hours at room temperature. The precipitate, which had formed, was filtered off and washed with water. After air drying the filter case was dissolved in chloroform (200 ml.) and the solution treated with solid sodium carbonate, aluminium oxide and activated charcoal. The solvent was then exchanged for ether and the material, which crystallized, was collected by filtration, m.p. 199°–201°.

Step B: Preparation of 10-(p-fluoro-phenyl)-2,3-dihydro-imidazo[2,1-b]quinazolin-5(10H)-one A solution of 5.4 g. of N-(p-fluoro-phenyl)isatoic anhydride, 2.5 g. of 2-methylmercapto-imidazoline and one pellet (about 100 mg.) sodium hydroxide in 75 ml. of dioxane is refluxed with stirring for 4 hours. The resulting mixture is evaporated to dryness, the residue dissolved in methylene chloride, washed with water and extracted twice with 1N hydrochloric acid. The combined aqueous extracts are washed with methylene chloride and then with diethyl ether and made basic with sodium bicarbonate. The resulting precipitate is filtered off, washed thoroughly with water, dried by suction, dissolved in methylene chloride, dried with sodium sulfate, treated with charcoal and the methylene chloride exchanged for methanol to crystallize 10-(p-fluoro-phenyl)-2,3-dihydro-imidazo[2,1-b]quinazolin-5(10H)-one, m.p. 278°–280°C.

EXAMPLE 13

The following compounds of the invention are prepared employing the reaction which is exemplified in Example 12.

A. 2,3-dihydro-10-phenyl-imidazo[2,1-b]quinazolin-5(10H)-one, m.p. 297°–299°C.
B. 12-phenyl-2,3,4,5-tetrahydro-(12H)-diazepino[2,1-b]quinazolin-7-one, m.p. 181°–183°C.

What is claimed is:
1. The method of effecting bronchodilation in an animal in need of said treatment comprising administering to said animal a bronchodilating effective amount of a compound of the formula:

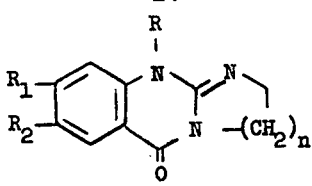

wherein
each of $R_1$ and $R_2$ is, independently, hydrogen, halo of atomic weight not greater than 36 or alkyl of 1 to 3 carbon atoms, or are either both hydroxy or both are alkoxy of 1 to 2 carbon atoms, or one is hydrogen and the other bromo, hydroxy or lower alkoxy of 1 to 2 carbon atoms,
$n$ is 1 to 3,
R is alkyl of 1 to 5 carbon atoms,

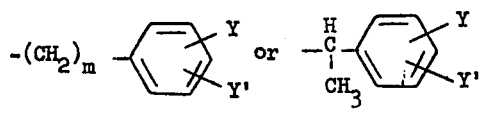

$m$ is 1 or 2,
each of Y and Y' is, independently, hydrogen, halo of atomic weight not greater than 36 or alkyl of 1 to 3 carbon atoms, or either both are hydroxy or both alkoxy of 1 to 2 carbon atoms, or one is hydrogen and the other bromo, hydroxy or alkoxy of 1 to 2 carbon atoms, provided that no more than two of $R_1$, $R_2$, Y and Y' are hydroxy, further provided that neither of $R_1$ and $R_2$ is hydroxy when either of Y and Y' is alkoxy and further provided that neither of Y and Y' is hydroxy when either of $R_1$ and $R_2$ is alkoxy,
or a pharmaceutically acceptable acid addition salt thereof.

2. The method of claim 1 in which the compound is a compound in which R is

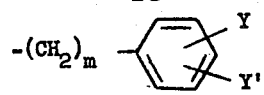

3. The method of claim 2 in which the compound is a compound in which each of $R_1$ and $R_2$ is hydrogen and $n$ and $m$ are each 1.

4. The method of claim 3 in which the compound is the compound 10-benzyl-2,3-dihydro-imidazo[2,1-b]quinazolin-5(10H)-one.

5. The method of claim 4 in which the compound is in free base form.

6. The method of claim 3 in which the compound is the compound 10-(4'-fluorobenzyl)-2,3-dihydro-imidazo[2,1-b]quinazolin-5(10H)-one.

7. The method of claim 6 in which the compound is in free base form.

8. The method of claim 6 in which the compound is in the form of hydrochloric acid addition salt.

9. The method of claim 2 in which the compound is a compound in which each of $R_1$ and $R_2$ is hydrogen, $n$ is 1 or 2, $m$ is 1, Y is halo at the 4-position and Y' is hydrogen.

10. The method of claim 9 in which the compound is a compound in which $n$ is 1.

11. The method of claim 9 in which the compound is 10-(4'-chlorobenzyl)-2,3-dihydro-imidazo[2,1-b]quinazolin-5(10H)-one.

12. The method of claim 9 in which the compound is 10-(4'-bromobenzyl)-2,3-dihydro-imidazo[2,1-b]quinazolin-5(10H)-one.

13. The method of claim 9 in which the compound is 11-(4'-fluorobenzyl)-2,3,4,11-tetrahydropyrimido[2,1-b]quinazolin-6-one.

14. The method of claim 1 in which the compound is administered in a daily amount of from 20 to 3000 milligrams.

* * * * *